US009993607B2

(12) United States Patent
Weaver et al.

(10) Patent No.: US 9,993,607 B2
(45) Date of Patent: Jun. 12, 2018

(54) ORAL CANNULA

(71) Applicants: Wendy Weaver, Arnold, MD (US); Glen Weaver, Murrysville, PA (US)

(72) Inventors: Wendy Weaver, Arnold, MD (US); Glen Weaver, Murrysville, PA (US)

(73) Assignee: Anesthemed, LLC, New Albany (*) Notice: Subject to any disclaimer, the term of this patent is extended or adjusted under 35 U.S.C. 154(b) by 360 days.

(21) Appl. No.: 14/498,006

(22) Filed: Sep. 26, 2014

(65) Prior Publication Data

US 2015/0099993 A1    Apr. 9, 2015

Related U.S. Application Data

(60) Provisional application No. 61/886,646, filed on Oct. 3, 2013, provisional application No. 62/009,522, filed on Jun. 9, 2014.

(51) Int. Cl.
| | |
|---|---|
| *A61M 16/08* | (2006.01) |
| *A61B 5/083* | (2006.01) |
| *A61M 16/04* | (2006.01) |
| *A61M 16/06* | (2006.01) |
| *A61B 5/00* | (2006.01) |
| *A61B 5/097* | (2006.01) |
| *A61M 16/10* | (2006.01) |

(52) U.S. Cl.
CPC ......... *A61M 16/085* (2014.02); *A61B 5/0836* (2013.01); *A61B 5/097* (2013.01); *A61B 5/4839* (2013.01); *A61M 16/0463* (2013.01); *A61M 16/0486* (2014.02); *A61M 16/0666* (2013.01); *A61M 16/1005* (2014.02); *A61M 16/0418* (2014.02); *A61M 16/0488* (2013.01); *A61M 2202/0007* (2013.01); *A61M 2202/0208* (2013.01); *A61M 2210/0625* (2013.01); *A61M 2230/432* (2013.01)

(58) Field of Classification Search
CPC ............ A61M 16/085; A61M 16/0486; A61M 16/1005; A61M 16/0463; A61M 16/0666; A61M 16/0418; A61M 16/0488; A61B 5/0836; A61B 5/097
See application file for complete search history.

(56) References Cited

U.S. PATENT DOCUMENTS

| | | | | |
|---|---|---|---|---|
| 3,590,820 | A | * | 7/1971 | Nehra ................... A61M 1/008 604/268 |
| 3,957,055 | A | * | 5/1976 | Linder .............. A61M 16/0488 128/200.26 |
| 4,595,005 | A | | 6/1986 | Jinotti |
| 4,662,871 | A | * | 5/1987 | Rafelson ............. A61M 1/0023 600/104 |
| 5,335,656 | A | | 8/1994 | Bowe et al. |

(Continued)

*Primary Examiner* — Tan-Uyen (Jackie) T Ho
*Assistant Examiner* — Jonathan Paciorek
(74) *Attorney, Agent, or Firm* — Luper Neidenthal & Logan; Michael Gallagher

(57) ABSTRACT

An oral cannula for delivering oxygen and sampling end-tidal carbon dioxide includes an oxygen supply lumen having plural outlets and an end-tidal carbon dioxide (ETCO2) lumen having an inlet. The ETCO2 lumen and oxygen supply lumen form a unitary oral cannula such that the oxygen supply lumen outlet is spaced apart from the ETCO2 lumen inlet. The oral cannula is adapted for bending or has a bend such that the oral cannula is insertable and retainable in a patient's mouth.

25 Claims, 13 Drawing Sheets

(56) References Cited

U.S. PATENT DOCUMENTS

| | | | |
|---|---|---|---|
| 5,544,648 A * | 8/1996 | Fischer, Jr. | ............ A61M 16/04 128/207.14 |
| 5,690,487 A * | 11/1997 | Whitehouse | ......... A61C 17/043 433/91 |
| 5,788,680 A * | 8/1998 | Linder | .............. A61M 25/0068 604/264 |
| 6,439,234 B1 | 8/2002 | Curti et al. | |
| 2005/0217678 A1 | 10/2005 | McCormick et al. | |
| 2007/0215162 A1 | 9/2007 | Glassenberg et al. | |
| 2010/0139664 A1 | 6/2010 | Curti et al. | |
| 2012/0209096 A1 | 8/2012 | Jaffe et al. | |
| 2012/0271187 A1 | 10/2012 | McNeill | |

\* cited by examiner

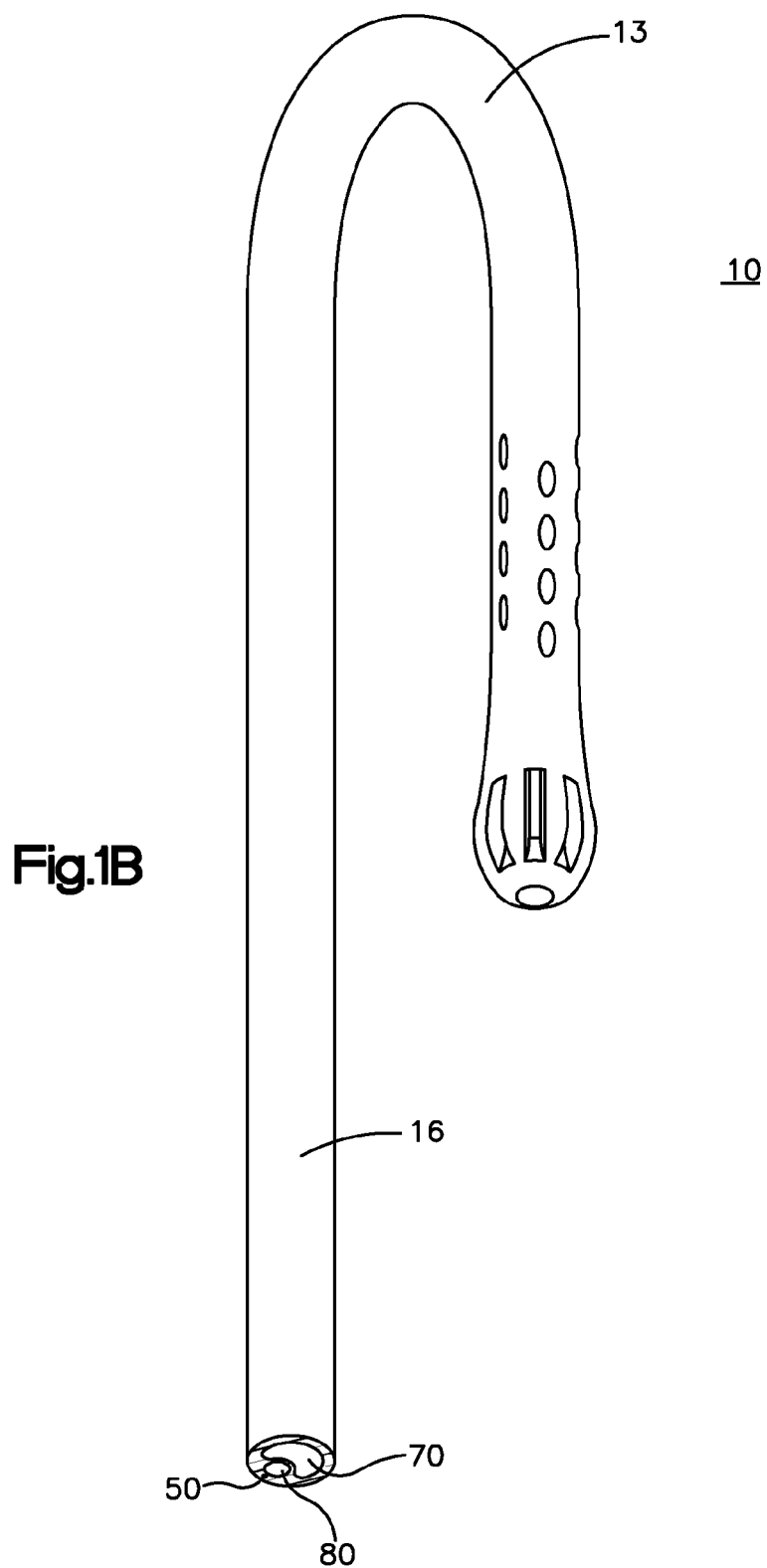

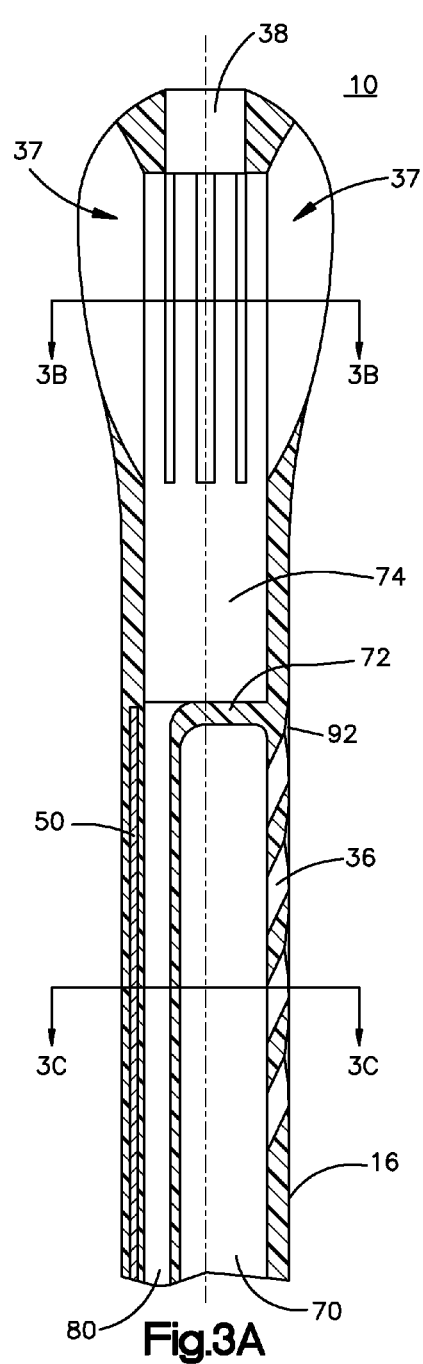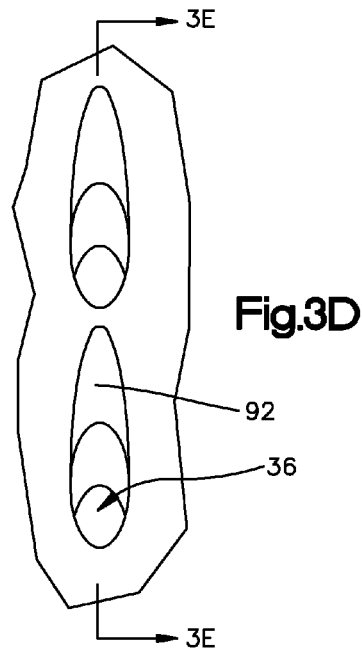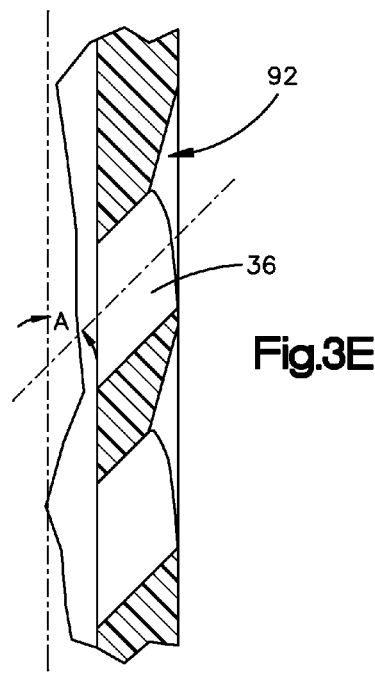

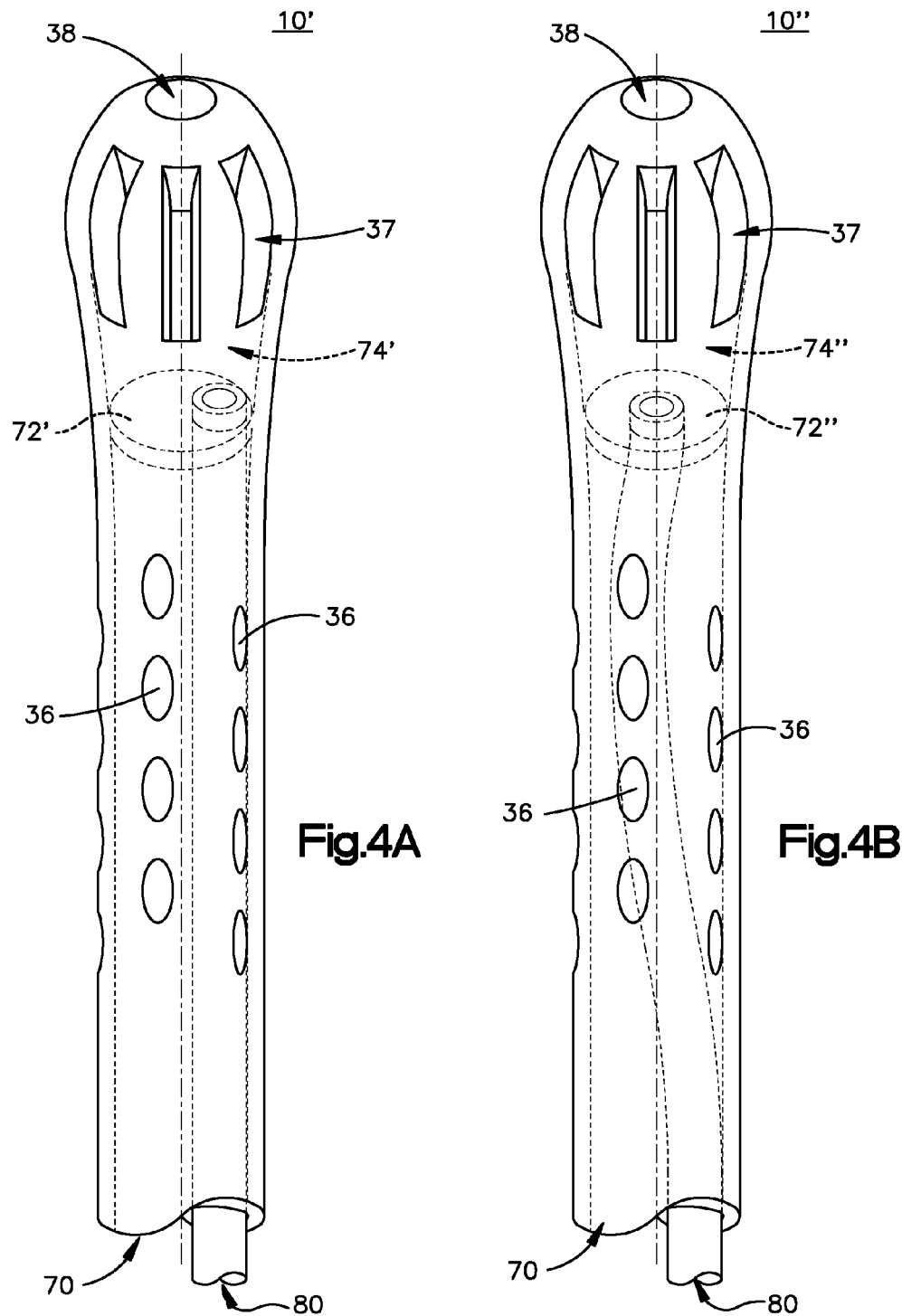

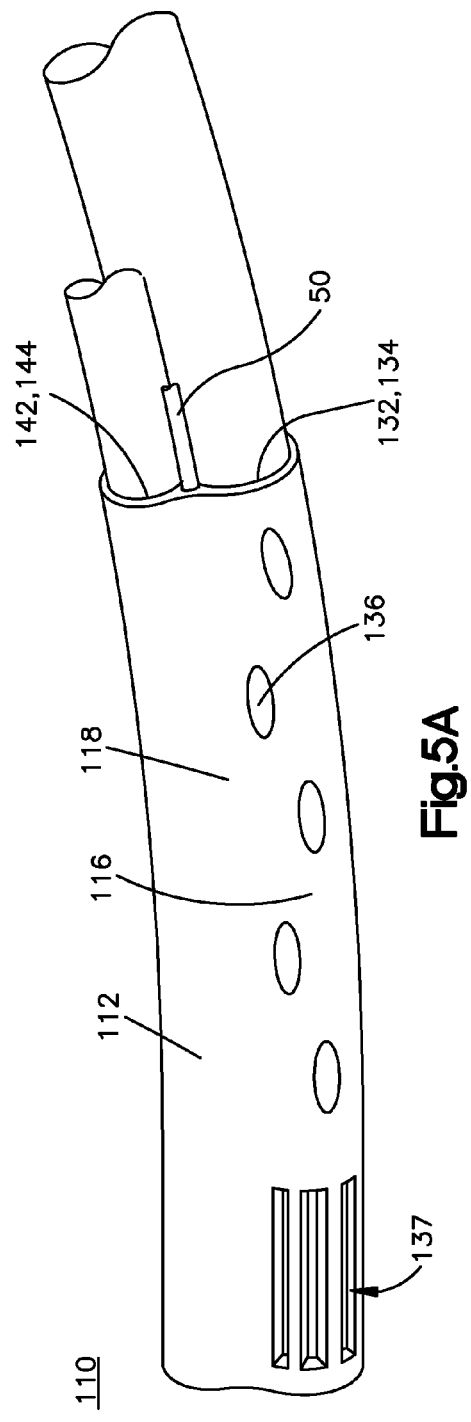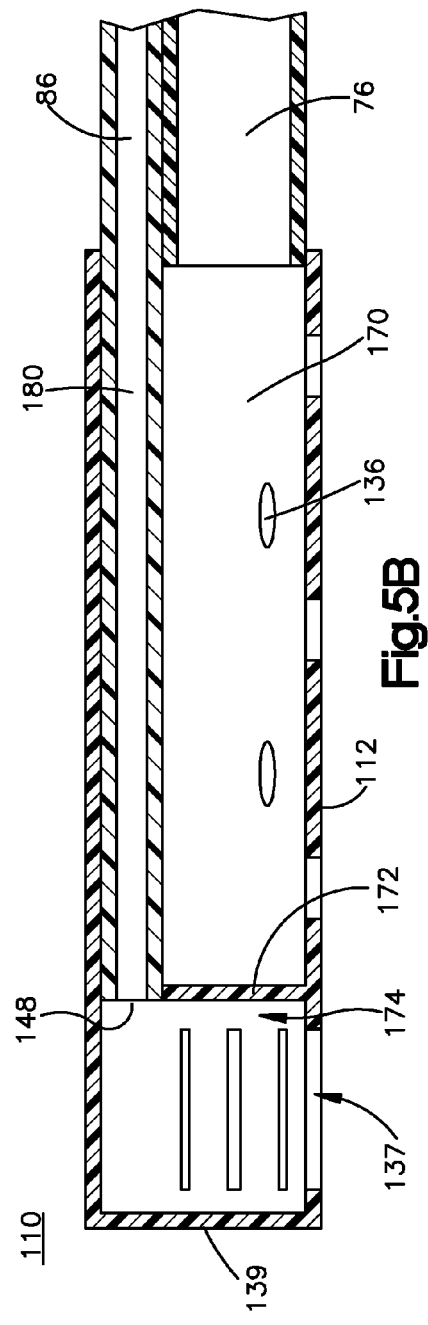

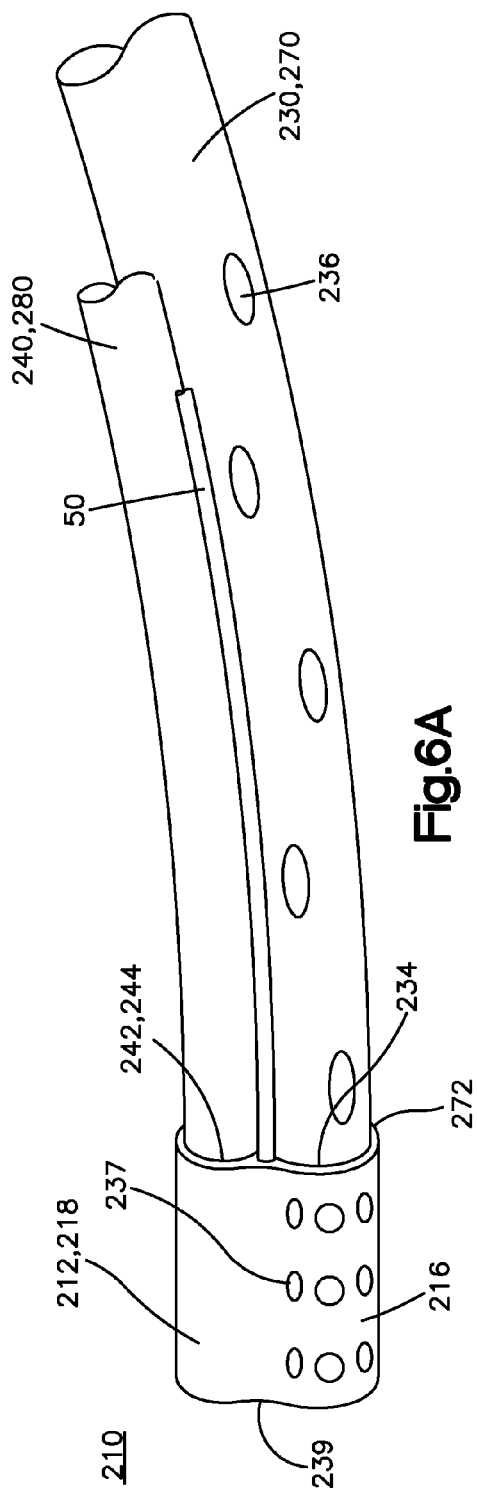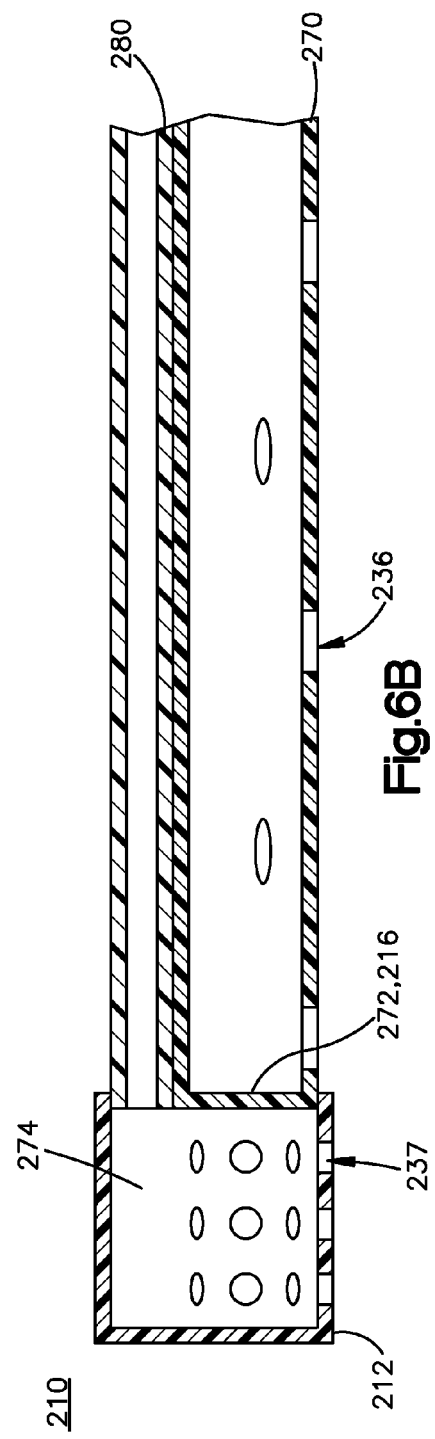

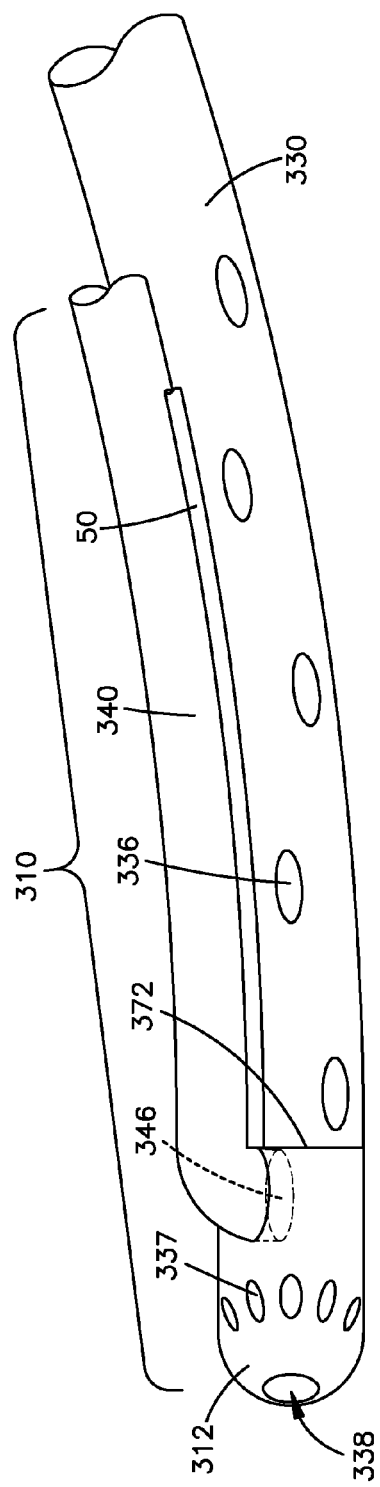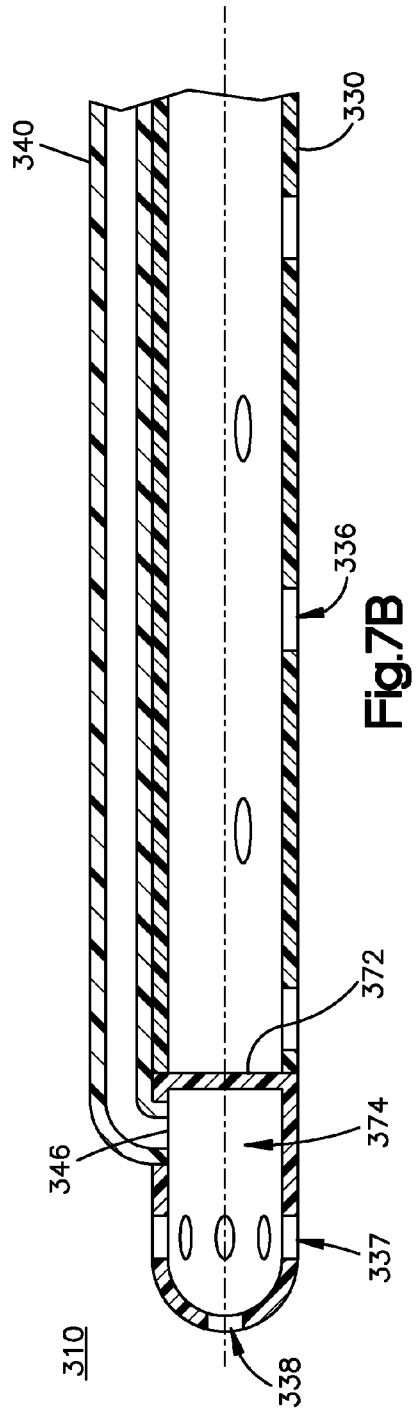

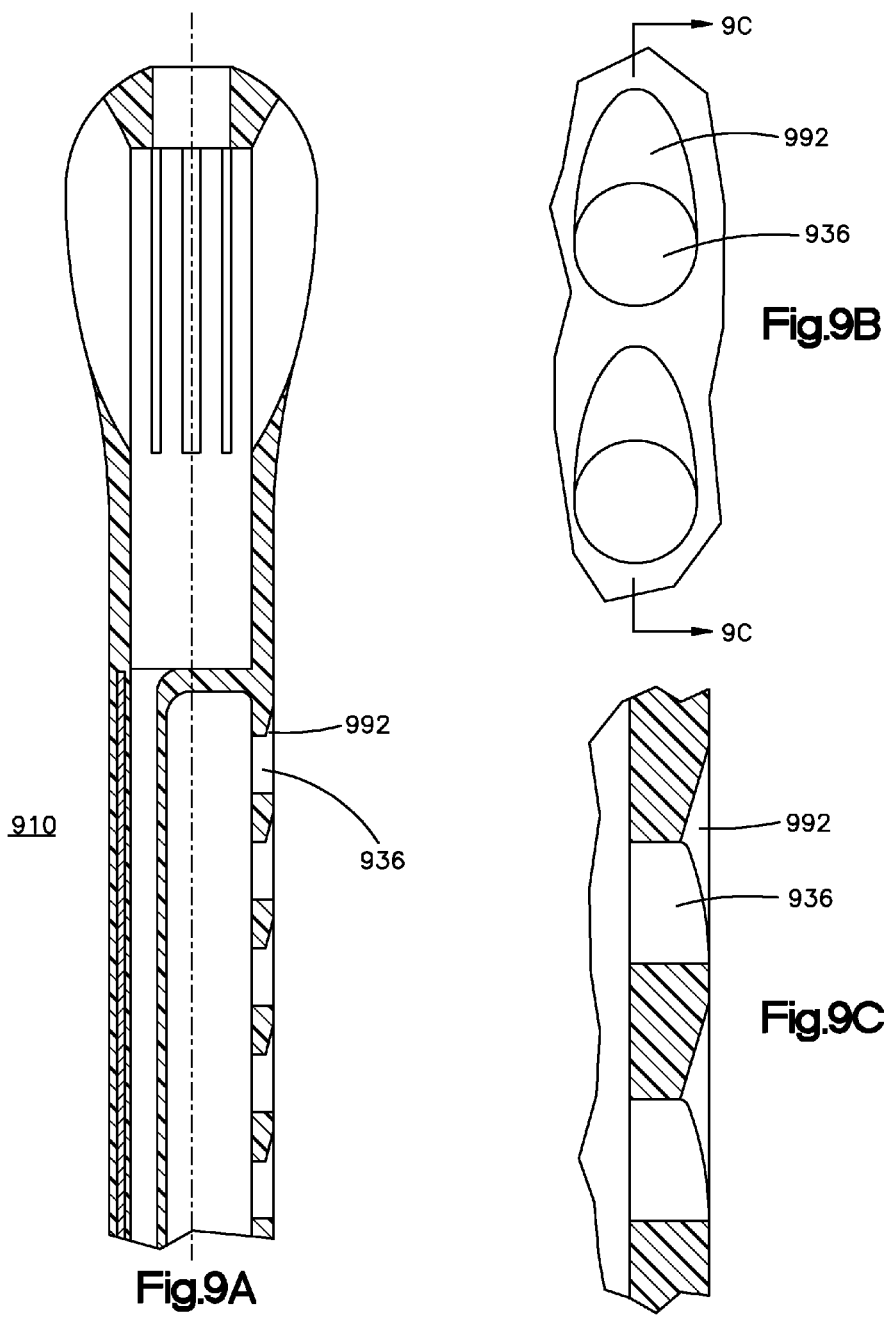

ORAL CANNULA

CROSS-REFERENCE TO RELATED APPLICATIONS

This application claims priority to U.S. Provisional Application No. 61/886,646, filed Oct. 3, 2013, and U.S. Provisional Application No. 62/009,522, filed Jun. 9, 2014, the disclosures of which are incorporated herein by reference in their entirety.

BACKGROUND

The present invention relates to medical devices and methods, and more particularly to medical devices and methods used while a patient is anesthetized.

Continuous monitoring of exhaled CO2, referred to as capnography, is the conventional standard of care for monitoring a patient's ventilation during operating room procedures. Capnography is also often used during non-intubated procedures that use moderate or deep sedation. A popular means for capnography is the well-known nasal cannula, such as disclosed in U.S. Pat. Nos. 5,335,656 and 6,439,234, which uses one nasal tube to supply oxygen to the sedated patient and another nasal tube to draw end-tidal CO2 for monitoring. A conventional Nasal Cannula (Adult) Salter Style® Ref 4707F from Salter Labs is packaged with several feet of side-by-side oxygen supply tubing and sampling lumen tubing, which terminates at individual, free tubes that are connected to opposing sides of the nasal cannula body.

Typically, the tubes connected to opposing ends of the nasal cannula are looped over the patient's ears, and then the tubes merge into a side-by-side configuration that extends to the oxygen supply and capnography system.

Under certain conditions, the sedated patient may receive insufficient oxygen through the nasal passages, such as when the nasal passages are blocked. An anesthetist might then place the nasal cannula in the patients mouth, such as through a portion of a bite block (if present), and increase the oxygen flow.

SUMMARY

As described herein, an oral cannula for delivering oxygen and sampling end-tidal carbon dioxide includes an oxygen supply lumen having plural outlets near a distal end of the oxygen supply lumen. The oral cannula also includes an end-tidal carbon dioxide (ETCO2) lumen having an inlet near a distal end of the ETCO2 lumen. The ETCO2 lumen and oxygen supply lumen form a unitary oral cannula such that the oxygen supply lumen outlet is spaced apart from the ETCO2 lumen inlet. The oral cannula is adapted for bending or has a bend such that the oral cannula is insertable and retainable in a patient's mouth.

In one embodiment, a method of administering oxygen and sampling end-tidal CO2 (ETCO2) for a patient includes a step of providing oxygen through an oxygen supply tube and through an outlet near a distal end of the oxygen supply tube. The method also includes a step of drawing a gas sample through an ETCO2 tube and through an inlet near a distal end of the ETCO2 tube. The ETCO2 tube is affixed to the oxygen supply tube to form a unitary oral cannula, such that the oxygen tube outlet is spaced apart from the ETCO2 inlet.

BRIEF DESCRIPTION OF THE FIGURES

FIG. 1B is an enlarged illustration of the oral cannula of FIG. 1A;

FIG. 3A is a longitudinal cross sectional view of the oral cannula of FIG. 2A;

FIG. 3D is an enlarged view of a portion of the sidewall of the oral cannula of FIG. 2A;

FIG. 3E is cross sectional view taken through lines 3E-3E of FIG. 3D;

FIG. 4A is a perspective view of a co-sheath lumen oral cannula, with hidden structure shown in dotted lines;

FIG. 4B is a perspective view of a coaxial lumen oral cannula, with hidden structure shown in dotted lines;

FIG. 5A is a perspective view of a side-by-side oral cannula;

FIG. 5B is a cross sectional view of the oral cannula of FIG. 5A;

FIG. 6A is a perspective view of another embodiment side-by-side oral cannula;

FIG. 6B is a cross sectional view of the oral cannula of FIG. 6A;

FIG. 7A is a perspective view of another embodiment side-by-side oral cannula;

FIG. 7B is a cross sectional view of the oral cannula of FIG. 7A;

FIG. 9A is a cross sectional view of an oral cannula illustrating another embodiment of aperture configuration;

FIG. 9B is an enlarged view of a portion of the sidewall of the oral cannula of FIG. 9A;

FIG. 9C is cross sectional view taken through lines 9C-9C of FIG. 9B;

DESCRIPTION OF PREFERRED EMBODIMENTS

The oral cannula embodiments described below have an oxygen supply lumen and an end-tidal carbon dioxide (ETCO2) sampling lumen. Each oral cannula is located or formed at the distal end of oxygen supply tubing and end-tidal carbon dioxide (ETCO2) sampling tubing, which tubing is connected to a conventional capnography and oxygen supply and monitoring system at the end opposite the oral cannula. Conventional luer fittings may be used. Oxygen from the oxygen source (not shown in the figures) and controlled by the anesthetist or control system flows out through the oxygen supply lumen and exits through the oral cannula. Sampling gases are pulled through the oral cannula and the ETCO2 sampling lumen to the capnography system.

Figure 1A:
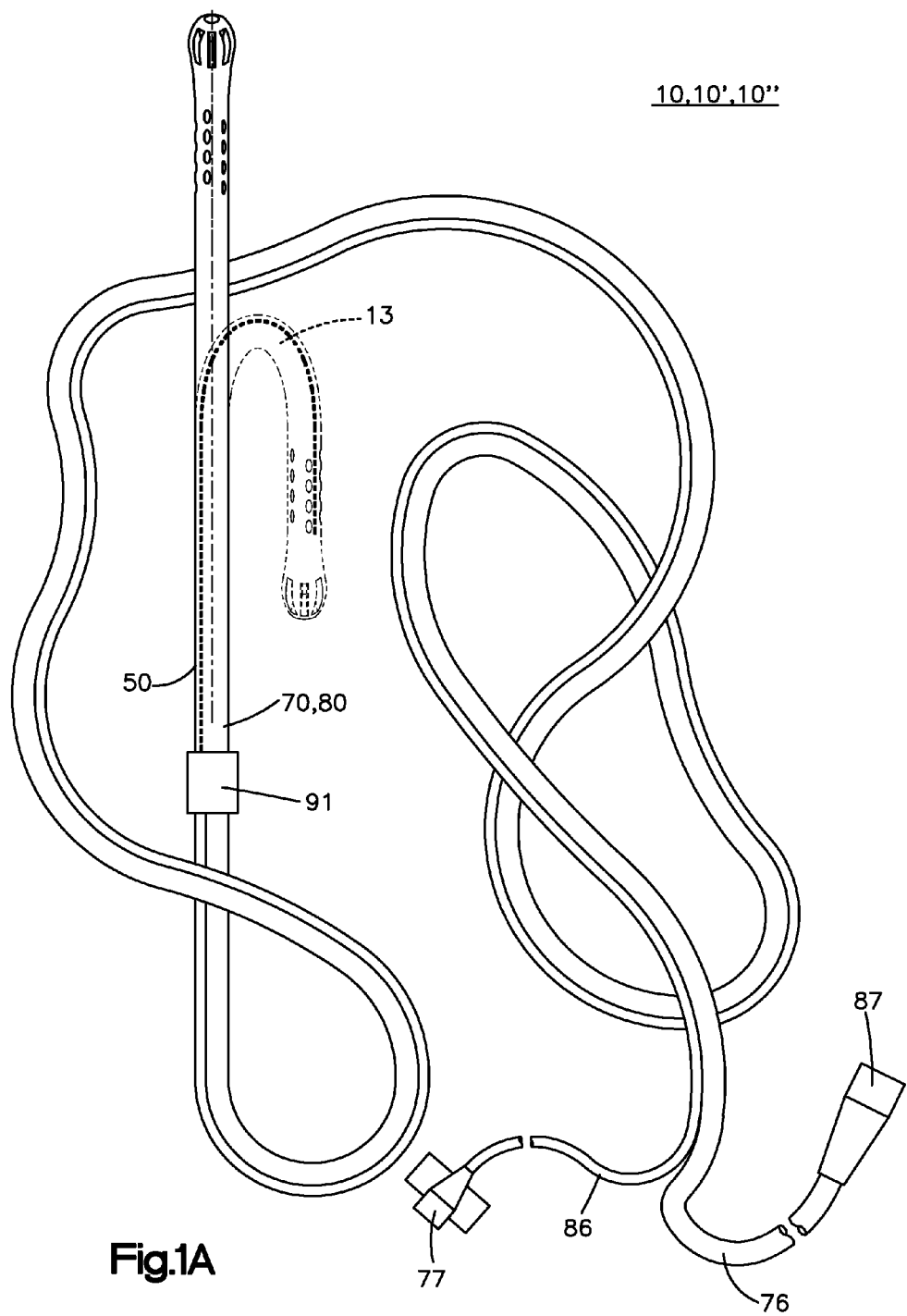
FIG. 1A is an illustration of an oral cannula and oxygen supply tubing and ETCO2 sampling tubing.
Figures 2A, 2B:
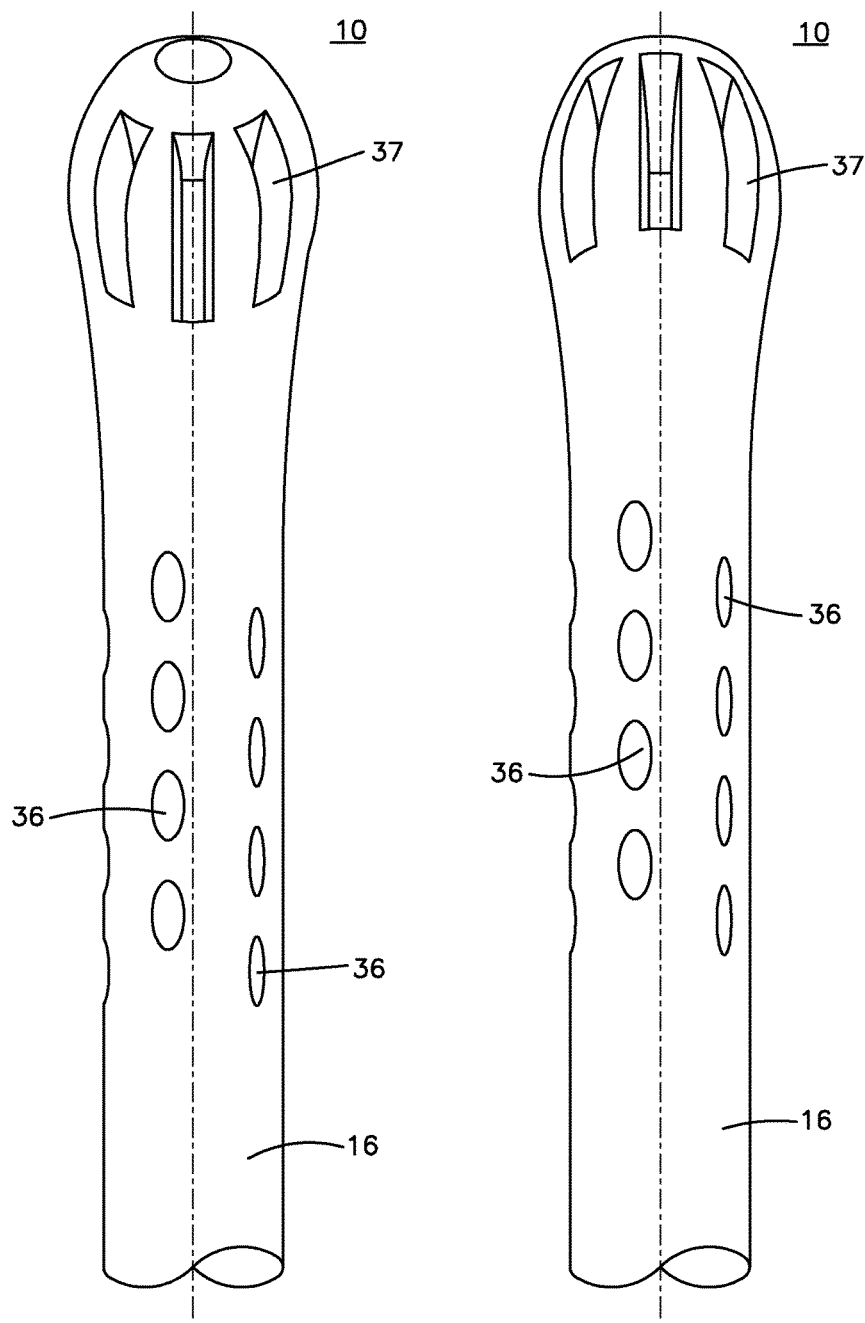
FIG. 2A is a perspective view of a an oral cannula according to a first embodiment.
FIG. 2B is an opposite perspective view of the oral cannula of FIG. 2A.
Figure 3B:
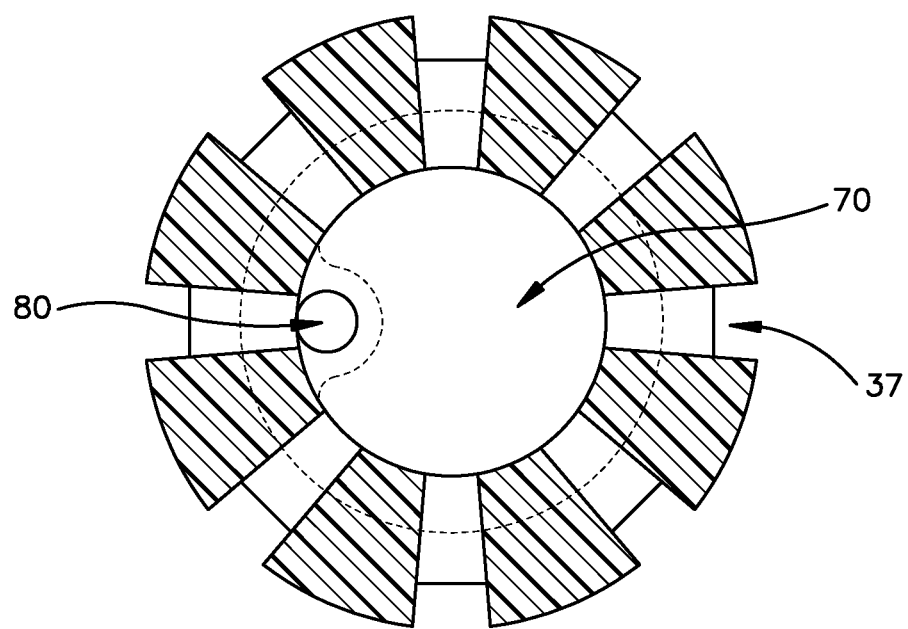
FIG. 3B is a transverse cross sectional view taken through lines 3B-3B in FIG. 3A.
Figure 3C:
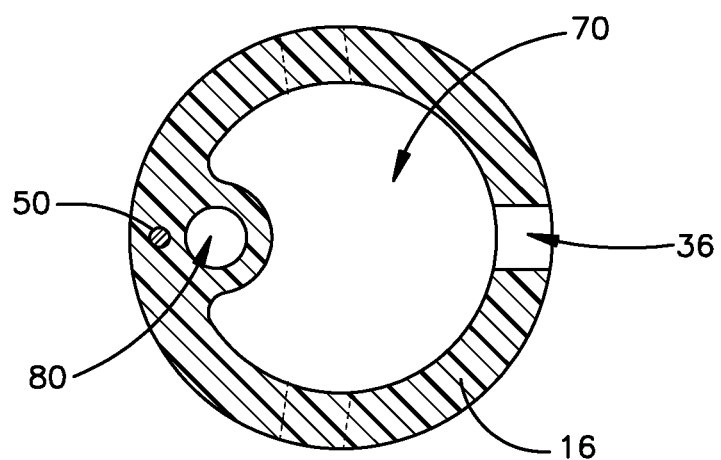
FIG. 3C is a transverse cross sectional view taken through lines 3C-3C in FIG. 3A.

FIGS. 1A and 1B illustrate an oral cannula that includes a first embodiment oral cannula 10, oxygen supply tubing 76, an end-tidal carbon dioxide (ETCO2) sampling tubing 86, and (preferably) conventional fittings 77 and 87 on respective proximal ends of the tubing. Oral cannula 10 includes an oxygen supply tube lumen 70 and ETCO2 sampling tube lumen 80. As shown in FIG. 1A, oxygen supply tube lumen 70 is at a distal portion of oxygen supply tubing 76; ETCO2 sampling tube lumen 80 is at a distal portion of sampling tubing 86. In this regard, a portion of the tubing forms the oral cannula, and another portion of the tubing is extraneous to the oral cannula and extends from the oral cannula. A connector 91 is illustrated schematically to encompass any kind of connection or structure for connecting tubing 76, 86 to lumens 70, 80.

The oxygen supply tube 76 and the ETCO2 sampling tube 86 (that is, the portions of the tubing that do not form the oral cannula 10 preferably are several feet long, affixed together in a side-by-side relationship, and terminate at conventional luer fittings 77, 87 suitable for connection to an oxygen supply and ETCO2 monitoring system. Alternatively, tubing 76 and 86 may be configured in a co-sheath or coaxial configuration.

Tubing 76 and 86 preferably are formed of conventional materials, such as those used for conventional nasal cannula. Among others, suitable plastics are available from Saint-Gobain Performance Plastics Corporation under the TYGON® SE-200 and TYGON name. This tubing has an inert liner and can be used as an O2 delivery line. Tubing 76 and 86 are side-by-side tubes that are affixed together along their entire length, with (preferably) the supply lumen being larger in diameter than the sampling lumen. Other embodiments of the oral cannula described below may have coaxial or other tubing configurations, but the function and materials of the supply and sampling tubing is the same for all embodiments. In this specification, the term "tubing" refers to conventional, flexible tubing (described more fully below); the term "lumen" refers to the structure or the passage formed by the structure of the inventive oral cannula.

As best shown in FIGS. 2A, 2B, and 3A through 3E, oxygen supply lumen 70 and ETCO2 sampling lumen 80 in the first embodiment are in a co-sheath configuration in which ETCO2 sampling lumen 80 is enclosed within oxygen supply lumen 70 to form a portion of oral cannula body 16. In this regard, the term "co-sheath" as used in this description refers to a structure in which one tube is contained within another, even if the axes of the tubes do not fall on the same line, including when inner tube is attached to an inner wall of the outer tube. The term "coaxial" as used in this description refers a structure in which tubes are oriented such that the longitudinal axes generally align, including when an inner tube is loose within the outer tube. A coaxial configuration is a subset of a co-sheath configuration.

Body 16 may be integrally formed with the tubing, or body 16 may be a unitary (that is, stand-alone) piece that has openings into which oxygen supply tubing 76 and ETCO2 sampling tubing 86 fit and are attached (including by a separate connector 91 to mate the parts). The sidewall of body 16 includes plural apertures 36 that are in communication with the interior of lumen 70 and tubing 76 such that oxygen supplied by the oxygen source (illustrated in FIG. 10A) and controlled by the anesthetist or control system flows out of oral cannula 10 through apertures 36. Body 16 also includes apertures 37, 38 that are in fluid communication with plenum 74, sampling lumen 80, and tubing 86, such that sampling can be controlled by the ETCO2 monitoring system. In this regard, a distal end of oxygen supply lumen 70 is sealed by a bulkhead 72 such that a distal end of the oral cannula distal to the bulkhead forms a plenum 74, as best shown in FIG. 3A. The portion of the oral cannula including the bulkhead and plenum can be referred to as a tip, such as a cap, for example, a bulb. In this regard, the term "tip" in this disclosure is used broadly to refer to any end structure. The tips may be formed of rigid plastic sleeve. Alternatively, the tips may be formed of a soft plastic.

FIG. 3D is an enlarged view of a portion of the sidewall of the oxygen supply lumen 70 illustrating a configuration of apertures 36. In this regard, apertures 36 define a centerline that forms an angle A from a longitudinal centerline, which is horizontal as oriented in FIGS. 3D and 3E. Preferably, angle A is between 25 and 75 degrees, more preferably between 40 and 60 degrees, and most preferably between 45 and 50 degrees. Further, a distal or upper portion of apertures 36 include a scoop 92 intended to inhibit unintentional blocking of the apertures by contact with a patient's tissues.

FIGS. 9A, 9B, and 9C illustrates an oral cannula 910 having apertures 936 that are oriented perpendicular to the sidewall. Apertures 936 includes a scoop at the distal end, which are intended to inhibit unintentional blocking of the apertures by contact with a patient's tissues. Scoops 92 and 992 are optional, as the present invention encompasses straight holes without scoops.

FIGS. 4A and 4B illustrate additional configurations of co-sheathed oral cannula. FIG. 4A illustrates oral cannula 10' having a bulkhead 72' that is a barrier that seals the end of supply lumen 70. Sampling lumen 80 protrudes through bulkhead 72' such that plenum 74 is connected to sampling lumen 80 and not in communication with supply lumen 70. FIG. 4B illustrates co-axial oral cannula 10" having a bulkhead 72", which functions the same as bulkhead 72'. Sampling lumen 80 protrudes through bulkhead 72" at or near the centerline of lumen 70.

Each bulkhead 72, 72', and 72" defines the corresponding plenum 74, 74', and 74". The text below will employ the reference numerals 72 and 74 to refer to any embodiment of the bulkhead and plenum for ease of description, and reference numeral 10 to refer to any of the embodiment in FIGS. 2A through 4B. Apertures 37 are formed in the plenum wall around the body of the plenum 74. An end aperture 38 may be formed at the distal-most end of oral cannula 10.

Oxygen from oxygen supply tubing 76 flows within supply lumen 70 on the outside of sampling lumen 80 to exit from apertures 36. Because bulkhead 72 forms the end of supply lumen 70, oxygen does not enter plenum 74. Rather, gas is pulled into plenum 74 through apertures 37 and 38 and through sampling lumen 80 by the action of the suction from the ETCO2 sampling system.

Body 16, as illustrated in FIG. 1B, has a bend 13 that may be (optionally) formed by a wire 50 or may be formed upon molding body 16, as explained more fully below. Body 16 can be formed of a rigid plastic or from a soft plastic, according to the particular design parameters of the oral cannula.

Figure 8A:
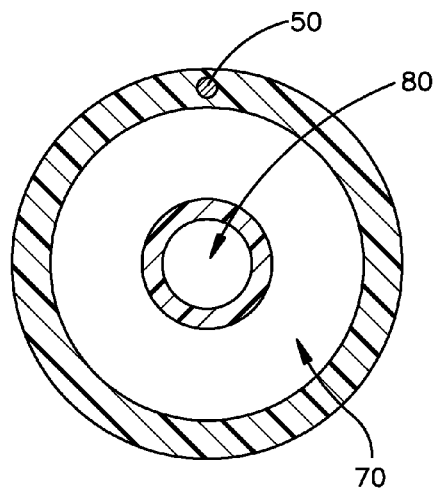
FIG. 8A is an enlarged cross sectional view of coaxial lumens of an oral cannula.
Figure 8B:
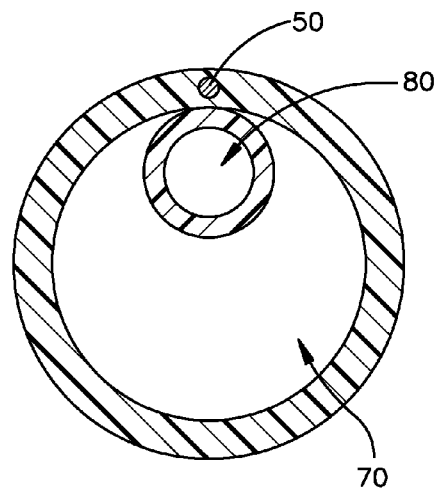
FIG. 8B is an enlarged cross sectional view of co-sheath lumens of an oral cannula.
Figure 8C:
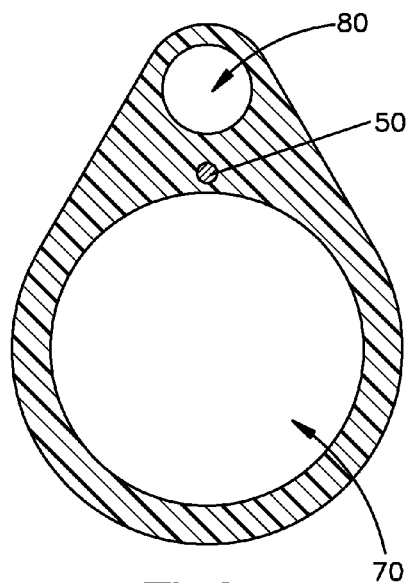
FIG. 8C is an enlarged cross sectional view of another configuration of co-sheath lumens of an oral cannula.
Figure 8D:
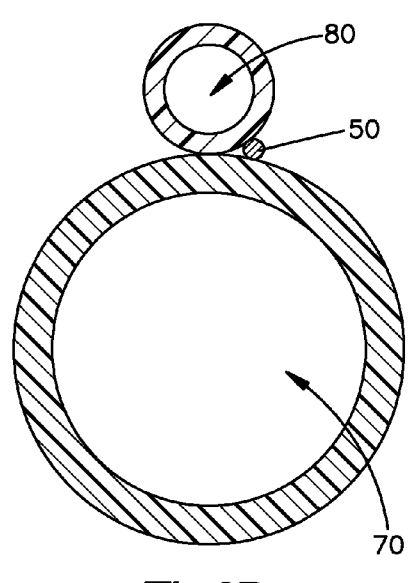
FIG. 8D is an enlarged cross sectional view of side-by-side lumens of an oral cannula.

FIG. 8A illustrates a common coaxial configuration in which the axes are or can lie literally on the same axis. The configuration of FIG. 8B is, in the nomenclature of this specification, also coaxial if the tube of lumen 80 is not attached to the tube of lumen 70, as the loose lumens will sometimes be coaxial. If the outside of lumen 70 is adhered to the inside of lumen 80 in FIG. 8, then the lumens have a co-sheath configuration. FIG. 8C illustrates another co-sheath configuration in which the outer sheath does not have a circulate cross section. FIG. 8D illustrates an oral cannula having a side-by-side (that is, not a co-sheath configuration).

FIGS. 5A and 5B illustrate an alternative embodiment oral cannula 110 including a tip 112, such as a cap. Tip 112 is formed by an elongate, supply body 116, such as a cylindrical or nearly cylindrical supply body, that forms an oxygen supply lumen 170 and a cylindrical, or nearly cylindrical sampling body 118 that forms an ETCO2 sampling lumen 180. Bodies 116 and 118 preferably are unitary (that is, formed of a single piece of plastic and are not detachable from one another) and side-by-side. Preferably, tip 112 preferably is approximately 1.0 to 3.0 inches long, preferably at least 1.5 inches long, and optionally includes a bend (not shown in FIGS. 5A and 5B), to house the entirety of the oxygen supply lumen and ETCO2 sampling lumens of the oral cannula. In this alternative, the tip would be connected to tubing 76 and 86, and the tip may be formed of a pre-bent rigid plastic, a pre-bent soft plastic, or be supplied with a shaping wire 50.

Oxygen supply lumen 170 has a proximal end 132 and a distal end 172. An opening 134 at proximal end 132 is sized to receive oxygen supply tubing 76. Tubing 76 is inserted into opening 134 and preferably is adhered or welded by conventional means. The sidewall of the body 116 includes plural openings 134 that are in communication with the interior of lumen 170 and tubing 76 such that oxygen supplied by the oxygen source (not shown in Figure) and controlled by the anesthetist or control system flows out of oral cannula 10 through apertures 136. In this regard, the distal end 172 terminates at a barrier and is sealed such that no oxygen flows out of the distal end of the oral cannula parallel to the longitudinal axis of oral cannula 110 or into plenum 174 (explained below).

ETCO2 lumen 180 has a proximal end 142 and a distal end 148. An opening 144 at proximal end 142 is sized to receive ETCO2 sampling tube lumen 180. Lumen 180 is inserted into opening 144 and preferably is adhered or welded together by conventional means. The sidewall of the body 118 preferably has no apertures that open into sampling lumen 180. Rather, sampling body 118 distally extends past the distal end of the oxygen supply lumen 170 into a plenum 174. Sampling body 118 at plenum 174 has apertures 137 and (optionally) apertures on the distal end 139 of oral cannula 110 (not shown in FIG. 5). Apertures 137 preferably are distributed around the circumference or periphery of plenum 174 such that sampling apertures 137 are distal to all of oxygen supply apertures 136. Apertures 137 enable communication and flow through or near the end of body 118 into the interior of sampling lumen 180 and sampling tubing 86 when pulled by the ETCO2 monitoring system (not shown in the figures). Distal end 139 defines the distal end of oral cannula 110.

FIGS. 6A and 6B illustrate another side-by-side embodiment oral cannula 210 including a tip 212, an oxygen supply lumen 230, and an ETCO2 sampling lumen 240. Tip 212 is formed by a nearly cylindrical supply body 216 that forms a portion of oxygen supply lumen 230 and a cylindrical sampling body 218 that forms a portion of ETCO2 sampling lumen 240. Bodies 216 and 218 are unitary (that is, formed of a single piece of plastic and are not mutually detachable from one another) and side-by-side. Preferably, tip 212 is between 0.5 inches and 1.5 inches long (measured parallel to the longitudinal axis). In cross section or in an end view, lumens 230 and 240 form a figure eight.

In this regard, oxygen supply lumen 230 of the oral cannula 210 can be formed in part by tip 212 and oxygen supply lumen 270 (that is, a portion of tubing 76). The ETCO2 sampling lumen 240 of oral cannula 210 can be formed in part by tip 212 and sampling lumen 280 (that is, a portion of tubing 86). In other words, a portion of tubing 76 and 86 can form a portion of oral cannula 210. And a portion of tip 212 can form a portion of oral cannula 210. Alternatively, embodiment oral cannula 210 encompasses an oxygen supply lumen 230 that is short and/or includes only a fitting to close off the end of tubing. In the embodiment shown in FIGS. 6A and 6B, body 216 includes an opening recess 234 sized to receive oxygen supply tube lumen 270, which is inserted into the opening recess 234 and preferably is adhered or welded by conventional means. The sidewall of the tubing that forms supply lumen 270 includes plural apertures 236 that are in communication with the interior of lumen 270 and tubing 76 such that oxygen supplied by the oxygen source and controlled by the anesthetist or control system flows out of oral cannula 210 through apertures 236. In this regard, the distal end of the supply lumen 270 is sealed by body 216 at a seal 272.

ETCO2 lumen 240 of tip 212 has an opening 244 at proximal end 242 that is sized to receive ETCO2 sampling tube lumen 280. Lumen 280 is inserted into opening 244 and preferably is adhered or welded together by conventional means. Sampling body 218 distally extends past the distal end of the oxygen supply lumen 270 to form a plenum 274. Sampling body 218 has apertures 237 near its distal end 239 and (optionally) apertures on its distal end (not shown in FIG. 6). Apertures 237 preferably are distributed around the circumference or periphery of plenum 274 and the sampling apertures 237 are distal to all of oxygen supply apertures 236. Apertures 237 enable communication and flow through or near the end of body 218, in some circumstances making a right turn, into the interior of sampling lumen 240 and sampling tubing 86 when pulled by the ETCO2 monitoring system. Distal end 239 defines the distal end of oral cannula 210.

FIGS. 7A and 7B illustrate another side-by-side embodiment oral cannula 310 that includes a tip 312, such as a cap, for example a bulb, that may be formed of a unitary piece having openings into which oxygen supply tubing and ETCO2 sampling tubing fit and are attached or may formed integral with tubing 76 and 86.

Oral cannula 310 encompasses an oxygen supply lumen 330, an ETCO2 sampling lumen 340, a barrier 372, and a plenum 374. Tip 312 includes a port 346 that extends through the sidewall of a tip 312 on the distal side barrier 372 to communicate with plenum 374. Tip 312 forms plenum 374 and includes sampling apertures 337 and end aperture 338.

The sidewall of the lumen 330 includes plural apertures 336 that are in communication with the interior of supply lumen 330 to enable oxygen to flow out of oral cannula 310. Oxygen supply lumen 330 terminates at barrier 372. Sampling lumen 340 extends exterior of the supply lumen 330, through port 346. Alternatively (not shown), port 346 can be located on the proximal side of barrier 372 such that port 346 extends through supply lumen 330 to pierce barrier 372 in a configuration like that described for embodiments having a bulkhead. In another alternative (not shown), sampling lumen 340 may extend all the way through supply lumen 330 and terminate only in an aperture at the distal-most end portion of the oral cannula. The latter alternative does not require a bulkhead. Plenum apertures 337 and 338 enable gas to be drawn through apertures 337 and 338, plenum 374, port 346, sampling lumen 340, and into sampling tubing 86 (not shown in FIGS. 7A and 7B).

Oral cannula 310 may be pre-formed with a bend. Tip 312 can be formed of a rigid plastic or from a soft plastic, according to the particular design parameters of the oral cannula and in embodiments in which tip 312 is elongated (not shown), may include a bend, as described elsewhere in this disclosure. Tip 312 can be formed as a separate structure that is fused to lumens 330 and 340, formed integral with lumen 330 by closing its distal end, or by other means as understood by persons familiar with tubing technology.

For the side-by-side embodiments of FIGS. 5A through 7B, the oxygen supply tube 76 and the ETCO2 sampling tube 86 (that is, the portions of the tubing that do not form the oral cannula 110, 210, 310) preferably are several feet long, affixed together in a side-by-side relationship, and terminate at conventional luer fittings 77, 87 suitable for connection to an oxygen supply and ETCO2 monitoring system. Alternatively, tubing 76 and 86 may be configured in a coaxial configuration.

Tubing 76 and 86 preferably are formed of conventional materials, such as those used for conventional nasal cannula. Among others, suitable plastics are available from Saint-Gobain Performance Plastics Corporation under the TYGON® SE-200 and TYGON name. This tubing has an inert liner and can be used as an O2 delivery line. Tubing 76 and 86 are side-by-side tubes that are affixed together along their entire length, with (preferably) the supply lumen being larger in diameter than the sampling lumen. Other embodiments of the oral cannula described below may have coaxial or other tubing configurations, but the function and materials of the supply and sampling tubing is the same for all embodiments. In this specification, the term "tubing" refers to conventional, flexible tubing (described more fully below); the term "lumen" refers to the structure or the passage formed by the structure of the inventive oral cannula.

The oral cannula described herein can be molded with a bend that resists deformation, may be molded with a bend that is plastically deformable such that the shape of the oral cannula can be adjusted as desired by the anesthetist or other users, may be formed with a shaping wire encapsulated in the plastic, may be formed with a shaping wire exterior to and adhered or mechanically affixed to the body of the cannula, optionally with the wire protected by a protective sheath, or may include other mechanical support (as will be understood by persons familiar with deformable plastic medical devices). In embodiments in which the oral cannula is intended to be deformable, the oral cannula is intended to be deformed by a user's hands. In embodiments in which the oral cannula is intended to be rigid, the oral cannula is stiff enough to resist deformation by the force of a user's hands.

For any of the embodiments in which the oxygen supply lumen and ETCO2 sampling lumen are not fixed in a concentric, coaxial configuration and which have a bend, it is preferred that the sampling lumen be near the inside radius of the bend to enhance the area of the oxygen supply lumen wall that is available for oxygen supply apertures.

Figure 10A:
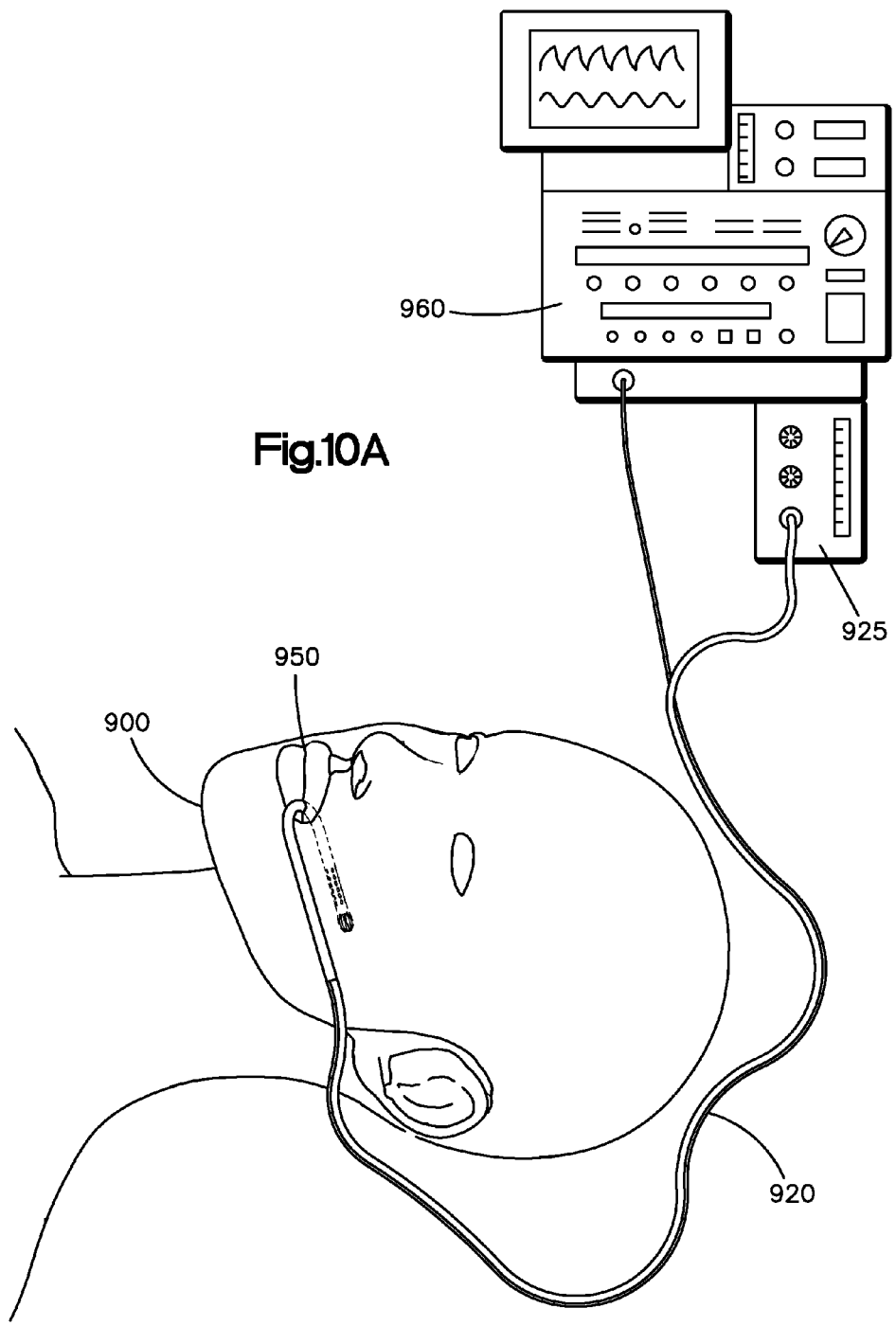
FIG. 10A is a schematic view of an oxygen supply and capnography system employing the present invention.
Figure 10B:
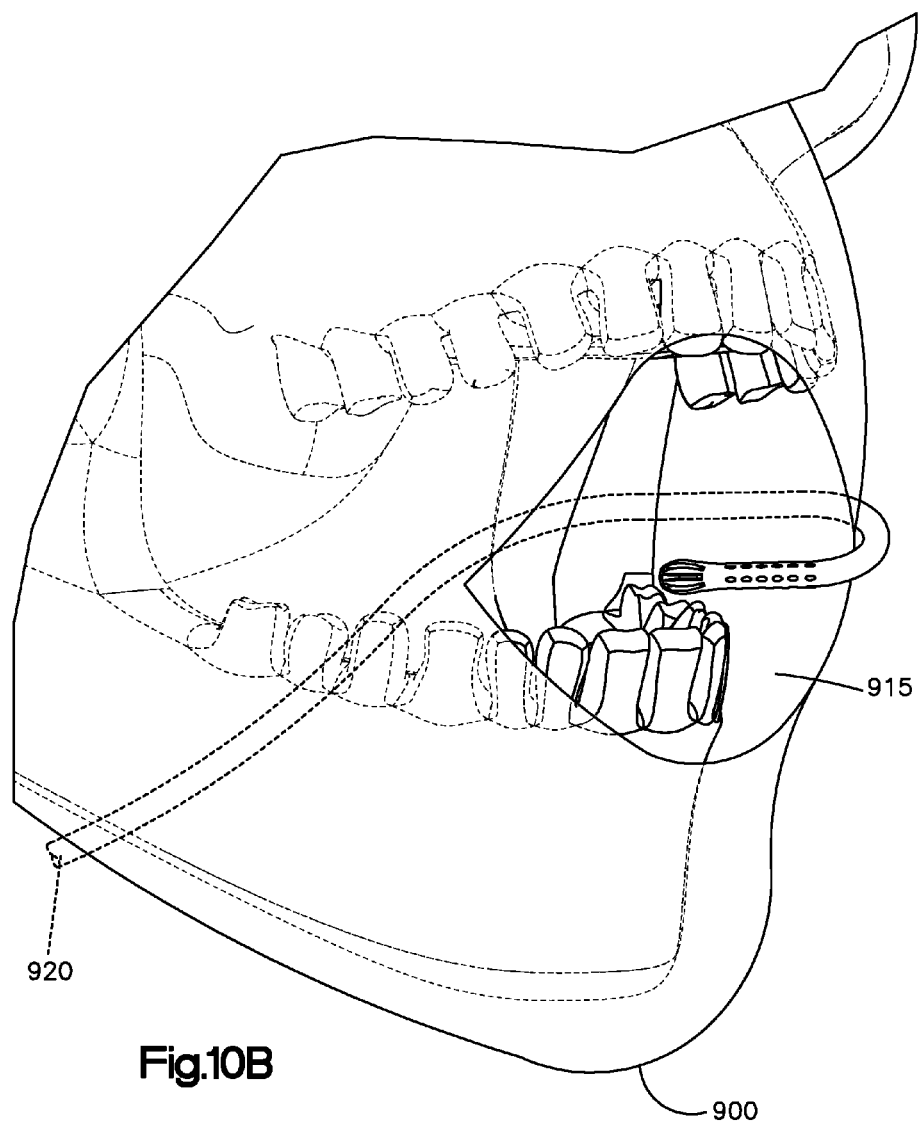
FIG. 10B is an enlarged schematic view of an oral cannula residing in a patient's mouth.

As illustrated schematically in FIGS. 10A and 10B, a patient 900 can have an oral cannula 10, which reference numeral is intended to represent any configuration herein, which is shaped and placed in his mouth 915. For convenience, only first embodiment oral cannula 10 is employed for the description of the overall system. The description of the system applies equally to other embodiments of the oral cannula. Also, while not shown in the figures, an oxygen delivery line 920 from an oxygen source 925 can be split, such as by a Y-splitter or other type of valve, into both an oral cannula line and a nasal cannula line. The nasal cannula line can run to a conventional nasal cannula (not shown), and the oral cannula can simultaneously be used as described above. Such a configuration may be advantageous for situations in which a patient stops breathing through his nose, but is still breathing through his mouth. An ETCO2 sampling line 950 can be connected to a patient monitoring system 960. The ETCO2 sampling line 950 can also be split.

The structure and function of the oral cannula described in this specification are for illustration purposes and are not intended to be limiting. Rather, it is intended that the claims be limited only to the express structure and function expressly stated in the claims. Further, features of the embodiments described above are not limited to the particular embodiment. Rather, the present invention encompasses any of the features described above in any combination.

What is claimed:

1. An oral cannula for delivering oxygen and sampling end-tidal carbon dioxide, the oral cannula comprising:
    an oxygen supply lumen having a proximal end, a distal end and an axial length and plural outlets near the distal end of the oxygen supply lumen, having a continuously non-retrograde oxygen flow path within the cannula for positively-pressurized oxygen-containing gas during operation, and oxygen exits the oral cannula into a patient during use only in a non-retrograde direction; and
    an end-tidal carbon dioxide (ETCO2) lumen having a proximal end, a distal end, and an axial length and a plurality of sampling inlets near the distal end of the ETCO2 lumen, the ETCO2 lumen and the oxygen supply lumen form a unitary oral cannula such that the oxygen supply lumen outlet is spaced proximally from the ETCO2 lumen inlet along the axial length of the oxygen supply lumen and the ETCO2 lumen,
    wherein the oral cannula is adapted for bending or has a bend such that the oral cannula is insertable and retainable in a patient's mouth.

2. The oral cannula of claim 1 further comprising a cap that forms at least a distal portion of the ETCO2 lumen.

3. The oral cannula of claim 1 wherein the oral cannula includes a cap that forms at least a portion of the oxygen supply lumen.

4. The oral cannula of claim 2 wherein the cap includes at least one sampling aperture near a distal end of the cap that opens into only the ETCO2 lumen, and includes oxygen supply outlets on a sidewall of the cap that open only into the oxygen supply lumen.

5. The oral cannula of claim 1 further comprising a bendable, shape-retaining support wire that is capable of being bent to form the bend.

6. The oral cannula of claim 1 wherein the oxygen supply lumen and ETCO2 lumen are side by side.

7. The oral cannula of claim 2 wherein the cap is a bulb that is coupled to a distal end of the oxygen supply lumen, the cap having at least one aperture that opens only into the ETCO2 lumen.

8. The oral cannula of claim 1 wherein the ETCO2 lumen extends though an outer tube wall of A plenum.

9. The oral cannula of claim 8 further comprising a fitting on the outer tube wall of the plenum such that the ETCO2 lumen extends though the outer tube wall of the plenum and opens into the fitting, the fitting is adapted to receive the ETCO2 sampling tube.

10. The oral cannula of claim 8 wherein the ETCO2 lumen extends through the outer tube throughout the length of the oral cannula and the ETCO2 lumen breaches a bulkhead to open into the plenum.

11. The oral cannula of claim 1 wherein the oxygen supply lumen and ETCO2 lumen are in a co-sheath configuration.

12. The oral cannula of claim 10 wherein a cap forms a least a portion of the ETCO2 lumen and at least a portion of the oxygen supply lumen, the cap having an aperture on a distal end of the cap the opens only into the ETCO2 lumen.

13. The oral cannula of claim 1 wherein a distal end of the oxygen supply lumen is sealed and the oxygen supply lumen includes outlets in a sidewall of the oxygen supply lumen.

14. The oral cannula of claim 1 wherein apertures selected from the group of apertures consisting of the outlets and the inlets include a scoop at a distal surface thereof.

15. The oral cannula of claim 1 wherein at least one of the apertures selected from the group of apertures consisting of the outlets and the inlet is non-orthogonal from the lumen supplying said aperture.

16. A method of administering oxygen and sampling end-tidal CO2 (ETCO2) for a patient, comprising the steps of:
providing oxygen through an oxygen supply tube having a continuously non-retrograde oxygen flow path within the oxygen supply tube for positively pressurized oxygen-containing gas and through an outlet near a distal end of the oxygen supply tube; wherein oxygen exits the oral cannula into a patient during use only in a non-retrograde direction; and
drawing a gas sample through an ETCO2 tube through an inlet located only distally to the distal end of the oxygen supply tube, wherein the ETCO2 tube is affixed to the oxygen supply tube to form a unitary oral cannula, such that the oxygen tube outlet is spaced only proximally from the ETCO2 inlet.

17. The method of claim 16 further comprising a step of bending the oral cannula such that the oral cannula is insertable and retainable in a patient's mouth.

18. The method of claim 17 wherein the step of bending includes bending a support wire.

19. The method of claim 16 wherein the step of providing oxygen includes providing oxygen through a cap that forms at least a portion of an oxygen supply lumen.

20. The method of claim 19 wherein the step of providing oxygen includes providing oxygen through oxygen supply apertures on a sidewall of the cap that open only into the oxygen supply lumen, and the step of drawing the gas sample includes drawing at least one sampling aperture near a distal end of the cap that opens into only the ETCO2 lumen.

21. The method of claim 19 wherein the cap is a bulb that is coupled to a distal end of the oxygen supply lumen, the bulb having at least one aperture that opens only into the ETCO2 lumen, such that the step of providing oxygen includes providing oxygen through the bulb, and the step of drawing the gas sample includes drawing the gas sample through the bulb.

22. The method of claim 16 further comprising a step of inserting and retaining the oxygen supply tube and the ETCO2 tube within a patient's mouth.

23. The cannula according to claim 1, having a non-co-sheath configuration wherein the oxygen supply lumen is at least partially contained within a separable first wall having an axial length and the ETCO2 lumen is at least partially contained within a separable second wall having an axial length, and the separable first wall and the separable second wall are joined for at least a portion of the axial length of both.

24. The cannula according to claim 23, wherein the first wall and the second wall and are separable by a user for at least a portion of the axial length of both the first and second wall.

25. An oral cannula for delivering oxygen and sampling end-tidal carbon dioxide, the oral cannula comprising:
an oxygen supply lumen having a proximal end, a distal end and an axial length and plural outlets near the distal end of the oxygen supply lumen, having a continuously non-retrograde oxygen flow path within the cannula for positively-pressurized oxygen-containing gas during operation; and
an end-tidal carbon dioxide (ETCO2) lumen having a proximal end, a distal end, and an axial length and a plurality of sampling inlets near the distal end of the ETCO2 lumen, the ETCO2 lumen and the oxygen supply lumen form a unitary oral cannula such that the oxygen supply lumen outlet is spaced proximally from the ETCO2 lumen inlet along the axial length of the oxygen supply lumen and the ETCO2 lumen, and oxygen exits the oral cannula into a patient during use only in a non-retrograde direction;
wherein the oral cannula is adapted for bending or has a bend such that the oral cannula is insertable and retainable in a patient's mouth.

* * * * *